United States Patent [19]

Smith

[11] Patent Number: 4,471,354
[45] Date of Patent: Sep. 11, 1984

[54] APPARATUS AND METHOD FOR REMOTELY MEASURING TEMPERATURE

[75] Inventor: Robert B. Smith, Loveland, Colo.

[73] Assignee: Marathon Medical Equipment Corporation, Loveland, Colo.

[21] Appl. No.: 324,124

[22] Filed: Nov. 23, 1981

[51] Int. Cl.³ .................. G08C 19/12; G08C 19/16
[52] U.S. Cl. ......................... 340/870.17; 128/631; 128/736; 128/903; 340/870.24; 374/183
[58] Field of Search ............... 340/870.17, 870.24, 340/870.2; 128/736, 631, 903; 374/179, 180, 183

[56] References Cited

U.S. PATENT DOCUMENTS

| | | | |
|---|---|---|---|
| 2,462,134 | 2/1949 | Scully . | |
| 3,453,546 | 7/1969 | Fryer | 128/903 |
| 3,534,728 | 10/1970 | Barrows | 128/631 |
| 3,609,728 | 9/1971 | Quinn et al. | 340/870.24 |
| 3,921,621 | 11/1975 | Baessler | 128/736 |
| 3,940,752 | 2/1976 | Bair | 340/870.24 |
| 3,971,362 | 7/1976 | Pope et al. | 128/736 |
| 4,321,933 | 3/1982 | Baessler | 128/736 |

Primary Examiner—James J. Groody
Attorney, Agent, or Firm—Yuter, Rosen & Dainow

[57] ABSTRACT

Apparatus and method for remotely measuring temperature in which a transmitter having a temperature sensitive element is placed in close proximity with the environment sought to the measured, with the temperature sensitive element controlling a reference voltage applied to a first terminal of a testing circuit, a second terminal of which receives a constant frequency alternating output of an oscillator. The output signal from the testing circuit is a constant frequency signal having a duty cycle which varies with the temperature of the element. An RF signal carrier is modulated at the transition points of the variable duty cycle signal for transmitting bursts of energy which are received and from which a replica signal corresponding to the variable duty cycle signal is reconstructed. A counter in the receiver counts high frequency pulses over a predetermined period of time during "on times" in duty cycle to obtain a numerical indication of the measured temperature.

9 Claims, 9 Drawing Figures

APPARATUS AND METHOD FOR REMOTELY MEASURING TEMPERATURE

BACKGROUND OF THE INVENTION

The invention disclosed and claimed herein relates to electronic thermometry. More specifically, the invention relates to apparatus for and method of measuring temperature with a monitor remote from the environment the temperature of which is sought to be measured and is adapted to receive temperature information from a transmitter in close thermal communication with such environment.

It is known in the art of clinical thermometry to use both glass and electronic thermometric devices. Both such known types of devices are inherently inaccurate, both lend themselves to cross-contamination, both devices are time-consuming to use and both require that the patient be awake or at least be disturbed while temperature is being taken. Even in monitoring the temperature of inanimate objects, present technology suffers from like deficiencies.

Prior art electronic thermometry has improved the art of thermometry, but still with certain disadvantages. For example, it is known in the art of remote electronic thermometry to vary the duty cycle of the waveform of electromagnetic energy transmitted indicative of temperature by employing a temprature sensitive element in close thermal communication with an environment, such as a human body, the temperature of which is sought to be measured, and to measure the duty cycle of the energy received by a monitor placed remotely from the subject whose temperature is to be measured to obtain an indication of the body temperature. Such thermometry systems generally employ a temperature sensitive circuit element such as a thermistor in the time constant circuit of a multivibrator to vary the duty cycle of the multivibrator as a function of temperature. Typical of such prior art arrangements are U.S. Pat. No. 3,453,546 to Fryer for Telemeter Adaptable For Implanting In an Animal, U.S. Pat. No. 3,921,621 to Baessler for Method And System Utilizing A Disposable Transmitter For Monitoring A Patient's Condition, U.S. Pat. No. 3,940,752 to Bair for Transducing System and U.S. Pat. No. 3,971,362 to Pope, et al for Miniature Ingestible Telemeter Devices To Measure Deep-Body Temperature. An inherent characteristic of the prior art remote thermometry systems which employ temperature variable time constant multivibrator circuits is a corresponding variation in the frequency as well as the duty cycle of the temperature information containing waveforms. Such systems are disadvantageous in requiring relatively broad transmission bandwidths and, hence, are susceptible to interference from spurious noise, harmonics and other transient effects. In addition, the monitor circuitry employed to receive the temperature information containing transmissions and to decode the transmissions into usable thermometry data are sometimes complex, expensive, and unreliable.

It is also known in the art to transmit information by varying the duty cycle of a constant frequency waveform for purposes of effecting remote control of an electrical device. Such a system is disclosed in U.S. Pat. No. 2,462,134 to Scully for Remote Control Arrangements. Such devices rely on the balancing of a transmitted waveform having a duty cycle indicative of the desired control with respect to a locally generated waveform derived from the functions to be controlled. While such arrangements are useful in obtaining a desired degree of control in an electromechanical system, they do not provide for the transmission and comprehension of intelligence such as thermometry data.

SUMMARY OF THE INVENTION

The present invention overcomes the aforesaid problems of the prior art in providing apparatus for remotely measuring temperature including a transmitter having a reference signal source, a periodic signal generator, a testing circuit connected to receive the output signals of the periodic signal generator and reference signal source, a temperature sensitive electrical element in thermal communication with the environment to be measured and connected in circuit with either the periodic signal generator or the reference signal source and having a characteristic with a magnitude which varies as a function of the temperature so as to produce a constant frequency signal having a duty cycle variable with the temperature of the temperature sensitive electrical element and means for radiating bursts of radio frequency electromagnetic energy in synchroniztion with the transitions of the variable duty cycle waveforms, and a receiver having means for detecting the transmitted bursts of energy, wave-shaping means for producing a signal having a waveform which is a replica of the variable duty cycle output of the testing circuit in the transmitter, a clock pulse generator for generation pulses at constant frequency substantially greater than the frequency of the replica signal, a first counter, means for applying the clock pulses to the first counter only when the replica signal is in the "on" portion of the duty cycle, means for periodically resetting the first counter, with the period after which the counter is reset being substantially greater than the period of the replica signal and means for displaying a count proportional to the count in the first counter which is proportional to the temperature being measured. In the preferred embodiment of the invention, each burst of transmitted energy comprises a predetermined number of pulses which are counted by a second counter in the receiver to verify the validity of the received transmissions. It is also preferred that the above-mentioned testing circuit be a comparator circuit, although other circuits might also be employed within the spirit and scope of the present invention.

It is therefore an object of the present invention to provide a remote thermometry system wherein RF transmissions are modulated by a fixed frequency waveform having a duty cycle variable with temperature.

Another object of the invention is to provide a system for remote thermometry wherein a replica of the variable duty cycle waveform developed by a temperature measuring circuit in a transmitter can be constructed from received bursts of transmitted RF electromagnetic energy corresponding to the transition points of the variable duty cycle waveform.

A further object of the invention is to provide a remote thermometry system wherein an indication of a transmitted temperature reading can be obtained from a variable duty cycle constant frequency waveform by counting higher constant frequency pulses for a fixed period of time only during "on" portions of the duty cycle.

Still a further object of the invention will be apparent from the following drawings and description of a preferred embodiment of the invention in which like reference numerals are used to indicate like parts in the various views.

DESCRIPTION OF THE PREFERRED EMBODIMENT

Figure 1:
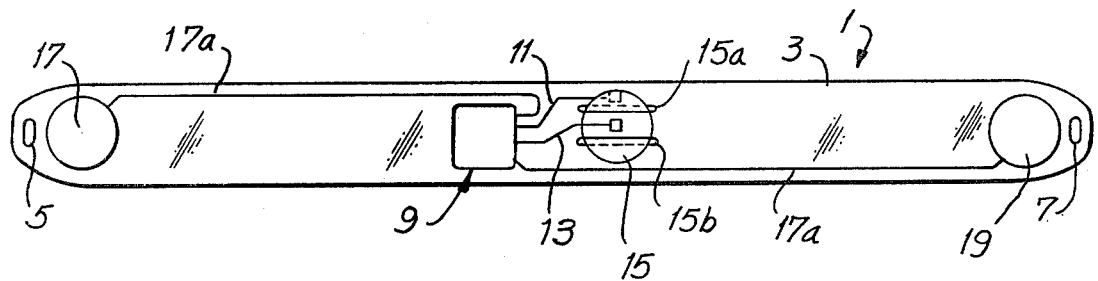
FIG. 1 is a plan view of a transmitter assembly adapted to be worn by a subject whose temperature is to be measured in accordance with the preferred embodiment of the invention.

Referring now to FIG. 1 of the drawings there is shown a preferred embodiment of a transmitter assembly suitable for use in hospitals, laboratories, zoos, or the like, in a remote thermometry system, in accordance with the invention. The transmitter assembly comprises a flexible printed circuit and includes a belt 3 having loops to retain mutually engageable fasteners 5 and 7 at either end. The size of the belt 3 can be suitable to fit around an object to be tested, where such attachment is desirable, with a temperature sensor housing 9 in close thermal communication with the environment generating the temperature sought to be measured. In the case where the transmitter assembly is to be used with neonatal patients, suitable means (not shown) may be provided for attaching the belt 3 across the chest and back of the patient. Of course, the transmitter assembly may also be adapted for use with inanimate objects of any configuration.

Mounted within the housing 9 is a temperature sensitive electrical element, which in the preferred embodiment of the invention is a thermistor having a resistance with a negative temperature coefficient, and an RF transmitter containing electronic circuitry for transmitting RF electromagnetic energy modulated with information indicative of the temperature detected by the unit. Conductors 11 and 13 extend between the electronic elements in housing 9 and a power source 15, such as a battery. Battery 15 is secured to the device in any conventional manner, although preferably flaps 15a, 15b receive the ends of battery 15 and hold it firmly in position thereat. Spring clips may be employed for this purpose.

A dipole antenna having sections 17 and 19 extends from housing 9, by conductors 17a, 19a, radiating the temperature modulated electromagnetic energy. Sections 17 and 19 are desireably of great surface area in comparison to the surface area of conductors 17a, 19a, at any given point along the surface of these conductors, as shown in FIG. 1. Of course, it will be recognized that configuration of Sections 17 and 19 is a matter of choice.

Figure 2:
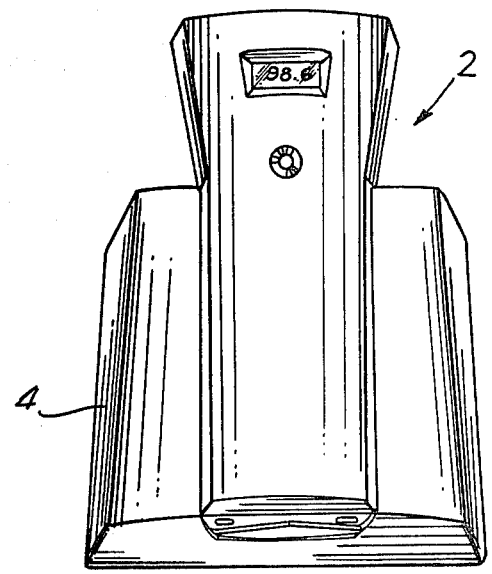
FIG. 2 is a perspective view of a receiver stored in a charging cradle in accordance with the preferred embodiment of the invention.

When the temperature sensor housing is placed in close thermal contact with a hospital patient, for example, the transmitter causes there to be radiated from antenna elements 17 and 19 a coded temperature signal. The transmitted signal is coupled at radio frequency to a receiver which derives from the signal a digital display of the patient's temperature. Receiver 2 is illustrated in FIG. 2, stored in charging cradle 4 which, in addition to providing storage for the receiver, preferably houses a battery charger for charging a battery within the receiver when stored and also houses a test transmitter for transmitting a test signal to the receiver for checking receiver accuracy.

In a hospital, for example, the transmitter belt 3 is preferably secured in the axillary area of a patient. The transmitter is held in place around the upper arm with elastic and a foam pad, or the like (not shown). Whether the belt is applied to an adult, as just described, or to pediatric and neonatal patients, as previously set forth, the sensor and transmitter housing are held against the skin and are thermally insulated.

With the transmitter thus attached to the patient for the duration of his stay in the hospital, a nurse can take the patient's temperature within one second whenever required. Once attached, and after reaching thermal equilibrium, there is no delay for rise time during which the sensor temperature must become stabilized at the patient's body temperature, which is the case in some prior art electronic thermometers since in the present invention the sensor is continuously worn by the patient and maintained at the patient's body temperature.

The transmitter assembly of FIG. 1 will now be described in greater detail with reference to FIG. 3.

In a preferred embodiment, within the temperature sensor housing 9 there is an oscillator 25, preferably 2.0 KHz, having a constant frequency, constant amplitude, triangle wave output signal which can be amplified in an amplifier 27 and then applied to one input terminal of a testing circuit 29, preferably a comparator. The other input of comparator 29 is connected directly to a thermistor 21 and to a series combination of a variable resistor 28 and the battery 15 both of which are in parallel with thermistor 21. Comparator 29 is responsive to the voltage across thermistor 21 and the voltage of the triangular waveform output of amplifier 27. If the voltage across thermistor 21 remains above the amplitude of the triangular waveform substantial current flow into the transmitter circuitry is inhibited. The thermistor and resistor network are preferably trimmed so that this will occur, for example, at a temperature below 89.6° F. This enhances shelf life of battery 15, which is preferably of the lithium type, since the transmitter assembly 1 is normally stored at room temperature well below the threshold turn-on temperature of the device. Since a hospitalized patient's body temperature will almost always be above 89.6° F., the transmitter circuitry will automatically be energized once the transmitter assembly 1 is applied to a patient and the thermistor 21 is stabilized at the patient's body temperature.

In a preferred embodiment, resistors 23 and 28 are laser trimmed to calibrate the transmitter so that the duty cycle of the output signal of comparator 29 corresponds to the temperature of thermistor 21, as will subsequently be explained. Once the transmitter is calibrated, the resistance of the variable resistors 23 and 28 remains substantially constant and only the resistance of thermistor 21 varies significantly with temperature. This variance in resistance is either direct or inverse, depending on design, although an inverse relationship is described herein. The circuit comprised of battery 15, resistor 28, and thermistor 21 form a reference signal source as a voltage divider network. As the temperature at thermistor 21 changes, the voltage across thermistor 21 varies inversely with the temperature change. This inverse voltage variation across thermistor 21 is then applied to comparator 29. When the output voltage from amplifier 27 exceeds the thermistor voltage applied to comparator 29, the output voltage from comparator 29 has a value which is low relative to the output voltage from comparator 29 when the output voltage of the amplifier 27 is less than the thermistor voltage applied to the comparator 29. The foregoing relates to a thermistor with a negative temperature coefficient. Use of a positive coefficient thermistor is also contemplated and would cause an expected reversal of the above discussed highs and lows, so that positively greater and less than would be understood as negatively greater and less than.

Figure 5A:
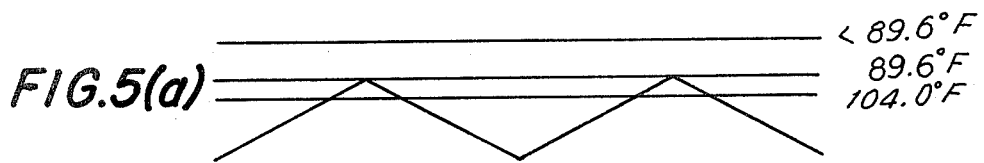
FIG. 5a–e is a common time base plot of various waveforms employed in the operation of the preferred embodiment of the invention.
Figure 5B:
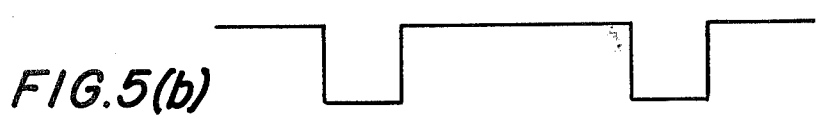

The effect of varying the thermistor voltage to the comparator 29 by changing the resistance of the thermistor 21 with temperature is seen in FIGS. 5a and 5b. FIG. 5b shows the output waveform of comparator 29 at 104.0° F. At temperatures less than 89.6° F., the bias voltage applied to comparator 29 from thermistor 21 exceeds the peak amplitude of the triangular waveform amplified voltage output from oscillator 25 and amplifier 27. Hence, at temperatures less than 89.6° F., the value of the output voltage of the comparator 29 is always high. If resistor 28 is set so that the bias voltage applied to comparator 29 is equal to the peak amplitude of the amplified triangular waveform output of amplifier 27 when thermistor 21 is at 89.6° F., the value of the output voltage of comparator 29 will momentarily go low each time the peak of the sawtooth waveform is reached thereby providing a constant-frequency cyclical waveform having extremely low duty cycle, that is, the "on time" or low value duration of the voltage output of comparator 29 will be extremely small relative to the "off time" or high value of the voltage output of comparator 29. As the temperature of thermistor 21 increases above 89.6° F., its resistance decreases and so too does the threshold voltage applied to comparator 29 so that the triangular voltage output of amplifier 27 exceeds the threshold voltage for a greater percentage of the triangular voltage cycle thereby increasing the duty cycle of the square wave output of comparator 29. The duty cycle is defined as the time when the triangular waveform voltage is greater than the threshold voltage. As seen in FIGS. 5a and 5b, when thermistor 21 is at a temperature of 104.0° F., the triangular waveform amplitude exceeds the amplitude of the threshold voltage for a duty cycle of approximately 25% of the duration of each cycle. This would therefore result in a square wave at the output of the comparator 29 having a duty cycle range up to 50% for the range of typical human body temperatures, for reasons which will later be explained, comparator 29 is connected so that the output of amplifier 27 is applied to the negative input and the thermistor voltage is applied to the positive input of comparator 29. This results in the inverted square wave shown in FIG. 5b at the output of the comparator 29 which still has the duty cycle of 25%, as defined above, at a temperature corresponding to 104° F. The output voltage signal from comparator 29 has a constant frequency and a periodic waveform corresponding to the frequency of the triangular wave oscillations derived from oscillator 25 and varies only in duty cycle in accordance with the temperature of thermistor 21. In addition, an RF pulse signature may be used to eliminate common RFI such as is produced by SCR light dimmers, etc., through the use of filters and electronic discrimination.

Figure 3:
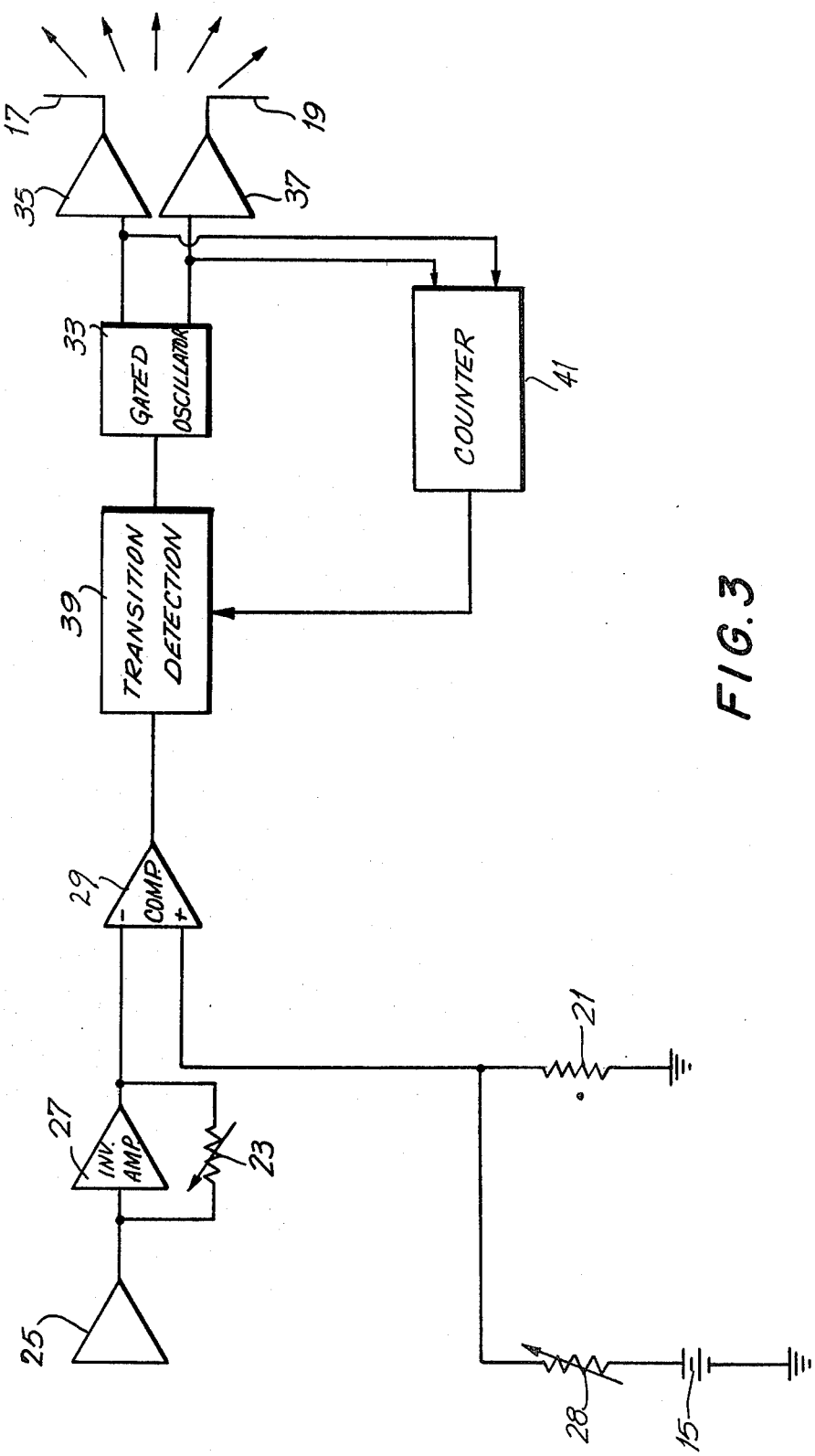
FIG. 3 is a schematic block diagram of the transmitted assembly shown in FIG. 1.

As seen in FIG. 3, in order to transmit the temperature measurement information contained in the duty cycle of the output waveform of comparator 29, a radio frequency carrier signal is modulated with signals concurrent with the transition points of the output waveform from comparator 29 between high and low, and low and high, values. For this purpose, a 2.0 MHz gated oscillator 33 generates square wave pulses at constant amplitude, constant frequency, and constant duty cycle which are applied to dipole antenna elements 17 and 19 through respective RF amplifiers 35 and 37. Transition detection circuit 39 normally inhibits the RF pulses from gated oscillator 33.

Transition detector circuit 39 connected between comparator 29 and gated oscillator circuit 33 detects each high to low and low to high amplitude transition of the variable duty cycle constant frequency output signal of comparator 29. Upon each detection of a transition in the variable duty cycle output of comparator 29, circuit 39 applies a signal to the gated oscillator circuit 33 to produce pulses which are transmitted to amplifiers 35 and 37, and thus to dipole antenna elements 17 and 19, so that the pulses of electromagnetic energy from gated oscillator 33 are radiated from antenna elements 17 and 19. This train of RF pulses is synchronized with the transition in the variable duty cycle output of comparator 29 so that the time relationship of the leading edge of the first RF pulse in each train with respect to the transition is constant. This provides greater accuracy in temperature measurement.

A counter circuit 41 counts the number of square wave pulses applied from gated oscillator 33 to antenna elements 17 and 19 and after a predetermined number of pulses is counted, applies a signal to transition detector circuit 39 to block subsequent pulses from gated oscillator 33 until the next transition in the constant frequency variable duty cycle output signal of comparator 29 is detected. Counter 41 divides the RF pulses out of gated oscillator 33 and provides a reset signal for transition detector 39. In the preferred embodiment of the invention, eight high frequency pulses are used, such that RF pulses from oscillator 33 are divided by 8, although other predetermined numbers of pulses can be used in accordance with the invention. Hence, there are radiated from members 17 and 19 of the dipole antenna bursts of electromagnetic energy with each burst including 8 sequential pulses having a frequency of 2.0 MHz. The bursts of energy radiated from transmitter unit 1 are received by receiver 2, illustrated in FIG. 2.

The function and operation of the receiver and its method of deriving temperature information from the transmitted bursts of electromagnetic energy from the transmitter, which corresponds to the transition points of the variable duty cycle constant frequency waveform output of comparator 29, will now be described with reference FIG. 4.

Figure 4:
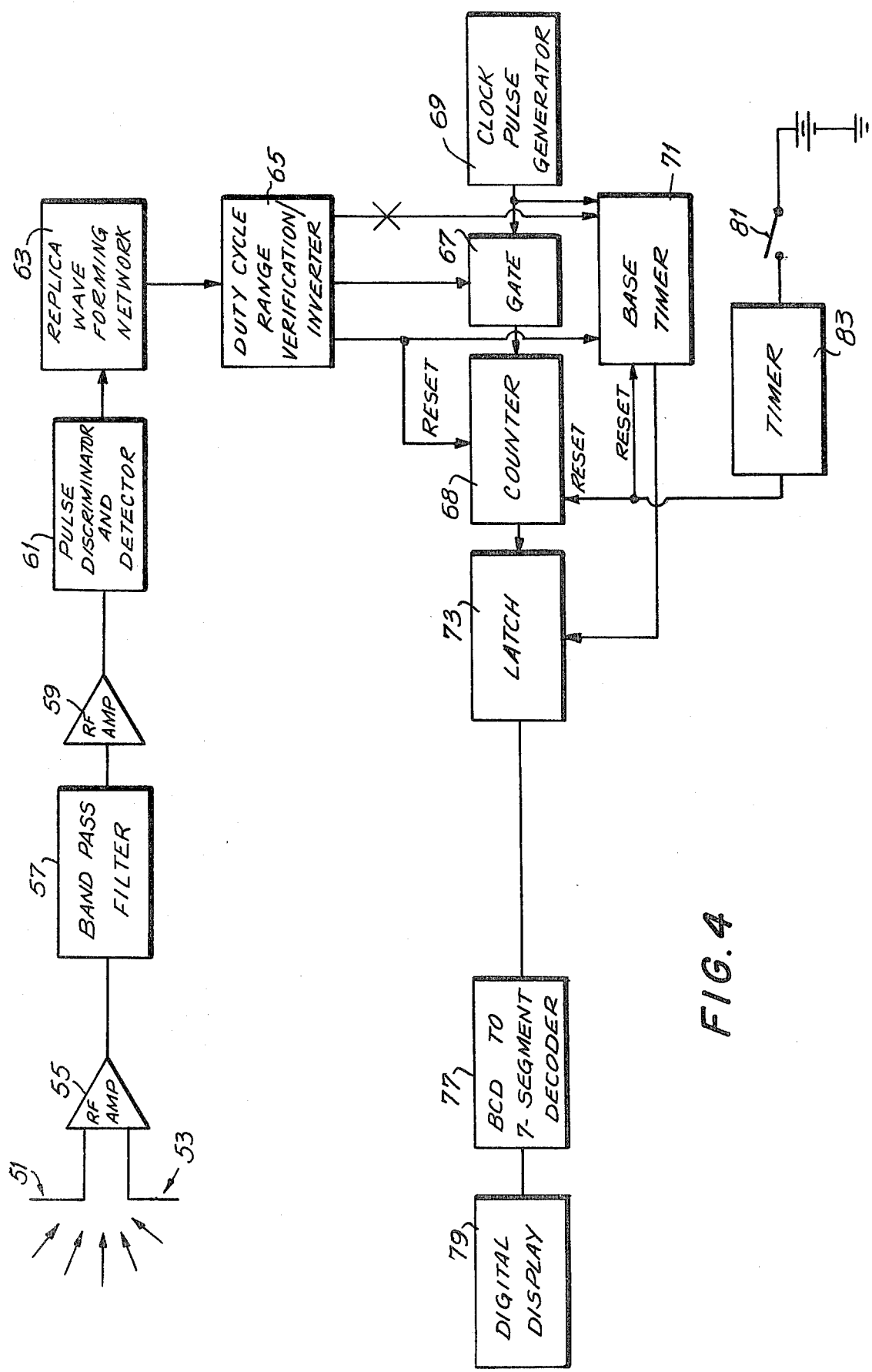
FIG. 4 is a schematic block diagram of the receiver illustrated in FIG. 2.

FIG. 4 is a schematic block diagram of a preferred embodiment of the electronic circuitry included within receiver 2. To take a temperature reading, a dipole antenna having elements 51 and 53 is placed within receiving range, for example approximatley 8 inches, of corresponding dipole elements 17 and 19 of the antenna in transmitter unit 1 to receive the bursts of RF electromagnetic energy transmitted by the transmitter coincident with the transition points of the variable duty cycle waveform output of comparator 29 in the transmitter. The received bursts of energy are amplified in RF amplifier 55 and then applied to a bandpass filter 57 which is tuned to a frequency of 2.0 MHz, the same as the frequency of gated oscillator 33 in the transmitter, and has a bandwidth preferably of 600 KHz. The Bandpass filter 57 screens out unwanted noise and other spurious signals and transients while permitting the high frequency RF energy transmission from transmitter 1 to be further amplified by RF amplifier 59 and then applied to a pulse discriminator and detector 61 which counts the number of pulses of each amplified burst of RF energy to determine whether the predetermined number of pulses, e.g. 8, are present. The pulse discriminator and detector 61 provides an output signal to a replica wave forming network 63 coincident with the string of high-frequency pulses constituting each energy burst for re-constructing a replica of the variable duty cycle constant frequency output signal of comparator 29.

The output of the replica wave forming network 63, which is a voltage signal having a waveform which is preferably an inverted replica of the voltage output of comparator 29, is applied to a duty-cycle range verification/inverter circuit 65 which compares the time between the first and second transition points of each cycle of the waveform with the time between the second and third transition points of the waveform to determine whether the duty cycle or "on time" is less than 50%, thereby signifying valid data only when the duty cycle is less than 50%. In the event that a duty cycle greater than 50% is encountered, a reset pulse is applied by duty cycle verification/inverter circuit 65 to counter 68 and base timer 71; duty cycle verification/ inverter circuit 65 also inverts the waveform. Counter 68 is used to derive a numerical determination of temperature and will presently be explained.

A duty cycle waveform signal is always applied to gate 67 from inverter 65. If the duty cycle range verification/ inverter circuit 65 finds the duty cycle of the waveform to be less than 50% it removes reset signals from counter 68 and timer 71. Counter 68 and timer 71 receives the output of 1 MHz clock pulse generator 69. This imputting to counter 68, however, is interposed by gate 67; enabling of gate 67 permits clock pulses from generator 69 to be applied to a count input of counter 68 only during the "on time" of the duty cycle of the replica signal output of replica wave forming network 63. By counting the number of clock pulses from clock pulse generator 69 during "on times" in the duty cycle of the replica signal over a fixed period of time, as determined by timer 71, a count which is representative of temperature corresponding to the duty cycle can be obtained. Timer 71 is actuated in response to the output signal of duty cycle range verification/inverter circuit 65 which indicates that the replica variable duty cycle is valid, and acts as a Fahrenheit or Celsius base counter. At this time, counter 68 begins counting clock pulses from generator 69 only during "on" portions of the duty cycle of the replica signal for 57.6 hundredths of a second (for Fahrenheit) or 32 hundreths of a second (for Celsius), at which time an output signal from timer 71 is applied to latch 73 for storing the then present count in counter 68. When a new temperature reading is required, counter 68 and timer 71 are instantaneously placed in the reset mode by activating push button 81. Counter 68 and timer 71 are also maintained in the reset mode by an output signal from duty cycle range verification/inverter circuit 65 when the duty cycle of the replica signal is not within the valid 0% to 50% range.

In a preferred embodiment, the count from counter 68 which is stored in latch 73 is in BCD format, and is applied to BCD to 7-segment decoder 77 to derive signals suitable for energizing appropriate segments of a 7-segment digital display 79 to provide a correct indication of patient temperature.

Counter 68 can include appropriate scaling circuitry so that the final count therein, which is stored in latch 73, is equal to the measured temperature. Additional scaling circuitry, not shown, can be employed to scale the count in counter 68, which is proportional to temperature, or a number which is equal to temperature.

Numerous cycles of the replica variable duty cycle signal are used in deriving temperature measurement. By employing a clock pulse generator 69 with a frequency which is substantially higher than the frequency of the replica variable duty cycle signal, and counting the pulses from the clock pulse generator 69 over a period substantially longer than the period of the replica variable duty cycle signal, a temperature measurement substantially free of the influence of anomalies can be obtained. Timer 71 also serves to eliminate some anomalies, such as pulse irregularities from generator 69, spikes from switch 81, and the like.

Figure 5C:
Figure 5D:
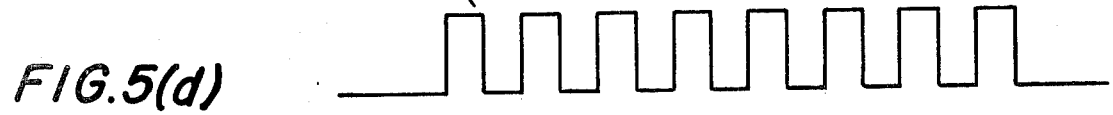
Figure 5E:

Referring to FIG. 5 of the drawings there is shown, in FIG. 5c on a time axis common with the variable duty cycle signal of FIG. 5b, the RF signal burst corresponding to the transition points of the variable duty signal of FIG. 5b. In FIG. 5d, there is shown on an extended time scale, the waveform of each burst of transmitted RF energy shown in FIG. 5c consisting of 8 sequential pulses having a constant frequency of 2.0 MHz. FIG. 5e illustrates the replica signal output of the replica waveforming network 63 in receiver 2 which is derived from the received burst of transmitted energy. The waveform in FIG. 5e, which is reconstructed in the receiver, is an inverted replica of the waveform of FIG. 5b taken from the output of comparator 29 in transmitter 1.

With transmitter 1 attached to the patient for the duration of his stay in the hospital, a nurse can take his temperature in approximately one second whenever a reading of the temperature is required. This is accomplished simply by bringing the receiver to within receiving range, for example, approximately 8 inches, of transmitter 1, thus RF coupling the receiver to the transmitter. The receiver is preferably provided with a "read temperature" button 81 which is pressed to energize the receiver electronics for reading the received temperature. When the button is momentarily actuated, the receiver electronics are energized. Timer 83 is provided, in a preferred embodiment of the invention, to maintain the receiver electronics energized for a short period after which the receiver automatically turns off. In the alternative, the receiver could be designed to turn off after receiving a valid RF signal and giving a reading thereof after a given period of seconds. The circuitry employed for turning the receiver off after a valid signal is received or after a time period will be known to those skilled in the art.

In a preferred embodiment, the receiver circuitry holds counter 68 in the reset mode until a valid signal is received. If the signal link between the transmitter and the receiver is broken or if radio interferences enters the receiver before the measurement is complete, the counter 68 is reset to prevent the display of an incorrect reading. If a valid signal is not received within, for example, 2 minutes, the receiver turns off by action of timer 83 until again actuated by depression of push button 81. The receiver may be recycled to obtain a new reading by reactuating push button 81.

After use is completed, the receiver is stored in the charging cradle 4 shown in FIG. 2. In one embodiment, the receiver is provided with an inductive coupling coil 5 to engage energy from a complimentary coil in the charging cradle in FIG. 2 to permit the batteries within the receiver to be recharged by battery charging circuits within charging cradle 4 and receiver 2. The charging circuit is conventional and therefore not described.

The charging cradle can also be provided with a "test transmitter" for transmitting a constant frequency signal to the receiver having a duty cycle corresponding to a predetermined temperature. In a preferred embodiment of the invention, the test temperature is 98.6° F., although any appropriate temperature could be so employed. Thus receiver accuracy can be established before and after a nurse makes her patient rounds.

In a preferred embodiment of the invention the transmitter is calibrated so that a temperature of 104° F. will result in transmitter comparator 29 generating a waveform having a duty cycle of 25%. Thus, a received transmitter signal representing 104° F. and timed for 0.576 clock seconds would result in 144,000 counted clock pulses from clock pulse generator 69. Of course, other like arrangements are also contemplated within the spirit and scope of the present invention.

By adjusting the triangular wave peak amplitude output of amplifier 27 so that it is always less than the termistor bias signal to comparator 29 when detecting a temperature below 89.6° F., the comparator can be prevented from switching at temperature below 89.6°. Preventing the comparator 29 from switching thereby inhibits all RF activity and reduces current drain from the power source, such as a 3-volt lithium battery, which powers the transmitter. This feature substantially enhances shelf life of the transmitter 1.

Although the invention has been described with respect to monitoring biological body temperatures, such as for humans or animals, it will be understood that the term body as employed herein is intended to refer to any subject, animate or inanimate, human or non-human, or any other form of heat radiator wherein remote monitoring is desired of local or ambient temperature. It is to be understood that the present invention is adaptable to any such use.

It will thus be seen that the objects of the invention have been accomplished. Because no information is contained in the pulse width modulation frequency, the transmitter radio frequency or the clock frequency, and because the receiver detection circuit is not sensitive to these frequencies, slight frequency variations from transmitter to transmitter or within a transmitter of in the receiver will not effect the system function.

What is claimed is:

1. Apparatus for transmitting temperature information to a remote receiver comprising
   a reference signal source means having an output,
   a periodic signal generator having an output,
   a testing circuit having inputs respectively connected to said periodic signal generator output and said reference signal source output and an output at which there is produced a signal having a characteristic with a first magnitude when the voltage at said periodic signal generator output is greater than the voltage at the output of said reference signal source and a second magnitude when the voltage at said periodic signal generator output is less than the voltage at the output of said reference signal source,
   a temperature sensitive element in thermal communication with the environment of which temperature is to be measured and connected in circuit with said reference signal source means, said element having a characteristic the magnitude of which varies as a function of its temperature, the voltage at a common connection point of said reference voltage source and said temperature sensitive electrical element being a function of said characteristic and defining said reference signal source output, and
   means connected to said testing circuit and responsive to said testing circuit output signal for radiating a burst of electromagnetic energy following each transition of said testing circuit output signal characteristic between said first and second magnitudes; and further comprising means for maintaining the peak amplitude value of said periodic signal below the amplitude of said reference signal when said temperature sensitive element is maintained at temperature below a predetermined range for preventing energization of said radiating means.

2. Apparatus of claim 1 wherein said testing circuit is a comparator.

3. Apparatus for receiving constant frequency variable duty cycle temperature information from a transmitter arranged to transmit energy burst signals relative to the temperature of a remote body; comprising:
   means for detecting burst of energy,
   signal forming means for producing a replica signal having a characteristic with a first magnitude during alternate intervals between said received burst of energy and a second magnitude during remaining intervals between said recceived bursts of energy,
   a clock pulse generator for generating pulses at a constant frequency of said replica signal,
   a first counter,
   means for applying said clock pulses to said first counter only when said replica signal characteristic has said first magnitude and
   means for periodically resetting said first counter, the resetting period being substantially greater than the period of said replica signal whereby the count in said first counter immediately prior to its resetting is proportional to the temperature of said remote body.

4. Apparatus according to claim 3 further comprising a band pass filter tuned to pass electromagnetic energy at frequencies near the frequency of said temperature information and to block frequencies deviating substantially therefrom.

5. Apparatus according to claim 3 further comprising means for determining whether the duty cycle of said replica signal is within a predetermined range, and
   means for resetting said first counter when the duty cycle of said replica signal is outside said range.

6. Apparatus according to claim 3 wherein said detecting means comprises means for counting the number of pulses contained in each burst of energy, and further comprising
   means for resetting said first counter when the duty cycle of said replica signal is greater than 50%.

7. Apparatus of claim 5 further comprising means for inverting said replica signal when said duty cycle is outside said range.

8. Apparatus for remotely measuring temperature comprising
   a transmitter including
   a reference signal source having an output,
   a periodic signal generator having an output,
   a testing circuit having inputs respectively connected to said periodic signal generator output and said reference signal source output, and an output at which there is produced a signal having a characteristic with a first magnitude when the voltage at said periodic signal generator output is greater than the voltage at the output of said reference signal source and a second magnitude when the voltage at said periodic signal generator output is less than the voltage at the output of said reference signal source,
   a temperature sensitive electrical element in thermal connection with a remote body of which temperature is to be measured and connected in circuit with one of said periodic signal generator and reference signal source, said element having a characteristic the magnitude of which varies as a function of its temperature, the voltage at the output of said periodic signal generator or said reference signal source being a function of said characteristic, and
   means connected to said testing circuit output and responsive to said testing circuit output signal for radiating a burst of electromagnetic energy following each transition of said testing circuit output signal characteristic between said first and second magnitude, and
   a receiver including
   means for detecting said bursts of energy,
   signal forming means for producing a replica signal having a characteristic with a first magnitude during alternate intervals between said received burst of energy and a second magnitude during remaining intervals between said received bursts of energy,
   a clock pulse generator for generating pulses at a constant frequency substantially greater than the frequency of said replica signal,
   a first counter,
   means for applying said clock pulses to said first counter only when said replica signal characteristic has said first magnitude, and
   means for periodically resetting said first counter, the resetting period being substantially greater than the period of said replica signal whereby the count in said counter immediately prior to its resetting is proportional to the temperature of said remote body.

9. A method for remotely measuring temperature comprising steps of applying a temperature sensitive circuit element in close thermal communication with the environment of which temperature is to be measured,
   connecting said temperature sensitive element to a source of reference voltage for varying the reference voltage as a function of sensed temperature;
   comparing the magnitude of said reference voltage with the amplitude of an alternating constant frequency signal,
   transmitting bursts of energy each time the amplitude of said alternating signal exceeds the magnitude of said reference signal,
   receiving said burst of energy, constructing a waveform having a duty cycle corresponding to said received bursts of energy, and
   counting constant high frequency signals over a predetermined period of time only during the "on time" of said duty cycle, said count being proportional to the temperature measure, and further comprising transmitting said bursts of energy as a predetermined number of high-frequency pulses,
   counting the number of pulses in each received burst of energy, and
   enabling the counting of said high-frequency signals only when the number of pulses in the received bursts corresponds to said predetermined number of pulses in said transmitted bursts.

* * * * *